United States Patent
Casset et al.

(10) Patent No.: US 6,487,451 B1
(45) Date of Patent: Nov. 26, 2002

(54) ACTIVE IMPLANTABLE MEDICAL DEVICE, IN PARTICULAR PACEMAKER, DEFIBRILLATOR OR CARDIOVERTER HAVING AUTOMATIC ADJUSTMENT OF THE STIMULATION PULSE AMPLITUDE

(75) Inventors: Cyril Casset, Paris (FR); Jean-Luc Bonnet, Montrouge (FR)

(73) Assignee: Ela Medical S.A., Montrouge (FR)

( * ) Notice: Subject to any disclaimer, the term of this patent is extended or adjusted under 35 U.S.C. 154(b) by 22 days.

(21) Appl. No.: 09/655,600

(22) Filed: Sep. 5, 2000

(30) Foreign Application Priority Data

Sep. 3, 1999 (FR) .......................................... 99 11045

(51) Int. Cl.$^7$ ................................................ A61N 1/18
(52) U.S. Cl. ..................................................... 607/28
(58) Field of Search ................................ 600/374, 509, 600/516, 517, 519; 607/5, 4, 9, 27, 28

(56) References Cited

U.S. PATENT DOCUMENTS

| 5,411,533 A | * | 5/1995 | Dubreuil et al. | 607/28 |
| 5,417,718 A | * | 5/1995 | Klels et al. | 607/28 |
| 5,766,230 A | | 6/1998 | Routh et al. | 607/27 |
| 5,902,325 A | | 5/1999 | Condie et al. | 607/28 |

FOREIGN PATENT DOCUMENTS

| EP | 0 334 681 A3 | 9/1989 | A61N/1/365 |
| EP | 0 870 516 A3 | 10/1998 | A61N/1/37 |
| EP | 0 870 516 A2 | 10/1998 | A61N/1/37 |

* cited by examiner

*Primary Examiner*—George R. Evanisko
*Assistant Examiner*—Frances P. Oropeza
(74) *Attorney, Agent, or Firm*—Orrick, Herrington & Sutcliffe LLP

(57) ABSTRACT

An active implantable medical device, in particular a pacemaker, defibrillator, or cardiovertor having an automatic adjustment of the stimulation pulse level. This device delivers to the heart stimulation pulses of low energy for the treatment of the cardiac disorders, which stimulation pulses present a predetermined amplitude and duration (width). The amplitude of the stimulation pulses can be automatically adjusted, a capture threshold is measured at predetermined intervals, and the measured capture threshold value is used as a basis for the adjustment of the stimulation pulse amplitude. The amplitude adjustment includes a validation of the measured capture threshold value, suitable to operate a coherence test between the last capture threshold value measured and at least one of the corresponding capture threshold values previously measured. The adjustment of the stimulation pulse amplitude level is then inhibited in the event of positive result of the coherence test.

9 Claims, 5 Drawing Sheets

ACTIVE IMPLANTABLE MEDICAL DEVICE, IN PARTICULAR PACEMAKER, DEFIBRILLATOR OR CARDIOVERTER HAVING AUTOMATIC ADJUSTMENT OF THE STIMULATION PULSE AMPLITUDE

FIELD OF THE INVENTION

The present invention relates to "active implantable medical devices" as defined by the Jun. 20, 1990 directive 90/385/CEE of the European Communities Council, more particularly to pacemaker, defibrillators and/or cardiovertors which are capable of delivering low-energy stimulation pulses to the heart for the treatment of the cardiac rate disorders, and even more particularly to the adjustment of the stimulation pulse amplitude (voltage level) over time.

BACKGROUND OF THE INVENTION

The voltage level (amplitude) used to stimulate the cardiac cavities (ventricular or atrial) of a human is a value typically selected in a range between 1.5 and 5.0 V (±10%), and which is adjustable in 0.25 V steps or increments within that range. The amplitude must be sufficiently high to cause the depolarization of the cavity myocardium (i.e., a stimulated heart beat). It is, however, important to avoid amplitudes that are too high to spare the lifespan of the battery, because the stimulation energy applied to the myocardium and, therefore, the corresponding consumption of the implant device, is proportional to the square of the amplitude (and also to the duration) of the stimulation pulse delivered.

Moreover, the capture threshold, i.e., the minimum energy level needed to cause a contraction of the myocardium, is a value which can vary over time. Thus, it is desirable to be able to reevaluate at regular intervals the stimulation amplitude level needed by operating a test of the threshold of the effectiveness of the stimulation, called the "capture threshold test" or more simply "capture test". The capture test thus determines the minimum amplitude needed to cause a stimulated heart beat.

The amplitude of the stimulation pulse is then adjusted on the basis of the capture threshold measured, and typically is a value that is twice the value of the measured capture threshold, subject to a minimum level (typically 1.5 V) and a maximum level (typically 5.0 V) amplitude. This provides a degree of confidence that the amplitude delivered will exceed the capture threshold and cause a beat.

International application WO-A-93/02741 and its corresponding U.S. Pat. No. 5,411,533 (commonly assigned herewith to Ela Medical S.A.) describe an automatic algorithm for testing the ventricular capture threshold, which is used in the Talent® model pacemaker marketed by Ela Medical. A clinical follow-up of patients equipped with this device revealed that, in certain cases, the algorithm of automatic capture threshold test will be deceived and give inaccurate measures, probably because of fusions (stimulations intervening in a concomitant way to a spontaneous QRS (ventricular) event) occurring at the time of the capture test.

These anomalies result in an overvaluation of the capture threshold compared to the real capture threshold of the patient. Because reevaluation of the capture threshold (and possible readjustment of the stimulation amplitude) is typically performed every six hours, an excessive amplitude level which is maintained for these six hours, although not in itself dangerous, is a source of overconsumption of battery energy, and thus leads to a reduction of the lifespan of the implant device.

OBJECTS AND SUMMARY OF THE INVENTION

It is, therefore, an object of the present invention to overcome the aforementioned disadvantage by proposing various improvements to the algorithm for the capture threshold test, so as to detect these anomalies which are likely to erratically occur, and to neutralize their effects when they occur.

Broadly, the present invention is directed to the type of implant device described by the above mentioned U.S. Pat. No. 5,411,533, which includes a stimulation means for delivering to the heart stimulation pulses of low energy for the treatment of the cardiac rate disorders, these stimulation pulses having a predetermined amplitude and a predetermined duration, and means for adjusting the amplitude of the stimulation pulses, comprising means for automatically measuring the capture threshold at predetermined intervals, and delivering a measured capture threshold value which can then be used as a basis for the adjustment of the stimulation amplitude.

According to the invention, the means for adjusting the amplitude also comprises means for validating the capture threshold value, suitable to operate a coherence test as between the last measured capture threshold value and a reference value which is a function of at least one of the corresponding capture threshold values measured previously. If the coherence test result is positive (i.e., incoherence exists), the adjustment of the stimulation pulse amplitude level is inhibited. In a preferred embodiment, the aforementioned reference value is one of the previously measured capture threshold values.

Preferably, the validating means produces a positive result of the coherence test when the difference between the last and the penultimate measured capture threshold values is higher than a first predetermined difference, and when the difference between the penultimate and the antepenultimate measured capture threshold values is less than a second predetermined difference. The aforementioned first or second difference is preferably equal to one step of the measurement of the capture threshold level, or an integer multiple of this step (i.e., an integer multiple for n an integer, $n \geq 1$). Further, the first predetermined difference is preferably greater than or equal to the second predetermined difference.

In another preferred embodiment, in the event of a positive result with the coherence test, the validating means starts a reiteration of the measurement of the capture threshold, the stimulation amplitude level being preferably adjusted after the reiteration on the basis of the lowest of the two capture thresholds thus measured, before and after the reiteration. In this last case, the device also includes means, responsive to the value of the capture threshold measured after the reiteration being higher than the one measured before the reiteration, for reducing the duration of the atrio-ventricular delay ("AVD"), and setting of the automatic measuring means of the capture threshold with this new value of the AVD.

The device also includes means, responsive to the automatic measuring means giving an indicator indicating the impossibility of delivering a result, to reduce the duration of the stimulation pulses, and setting of the automatic measuring means with this new value of the pulse duration.

BRIEF DESCRIPTION OF THE DRAWINGS

Additional features, characteristics and advantages of the present invention will appear to a person of ordinary skill in the art in view of the following detailed description, which is made with reference to the annexed drawings, in which.

DETAILED DESCRIPTION OF THE INVENTION

The capture threshold test algorithm described in WO-A-93/02741 and U.S. Pat. No. 5,411,533, and which is used in the commercial Talent pacemaker apparatus of ELA Medical, envisages to test the capture threshold of the ventricle every six hours, automatically. This test provides three possible results:

1) a "FAILURE" indicator, meaning that, because of aberrant results during the capture threshold test, the test cannot provide any value. In this case, the stimulation amplitude value is then fixed automatically to the maximum value of 5.0 V, for the following six hours.

2) a "RESEARCH" indicator, meaning that the capture threshold algorithm could not be implemented correctly. In this case, the conditions for launching the test were not fulfilled during the previous six hours (for example, because of a too fast rate or because of atrioextrasystoles), and the stimulation amplitude is then forced to the maximum value of 5.0 V, while the device attempts to launch the test again. If this situation is sustained for six hours, then the algorithm produces the "RESEARCH" indicator which is recorded in the statistics file of the pacemaker.

3) an "OK" indicator, with an associated measurement value corresponding to the last effective capture threshold found by the algorithm. This value is the one which will be memorized by the pacemaker (i.e., stored in memory) and used to define the ventricular stimulation amplitude for the next six hours.

Figure 1:
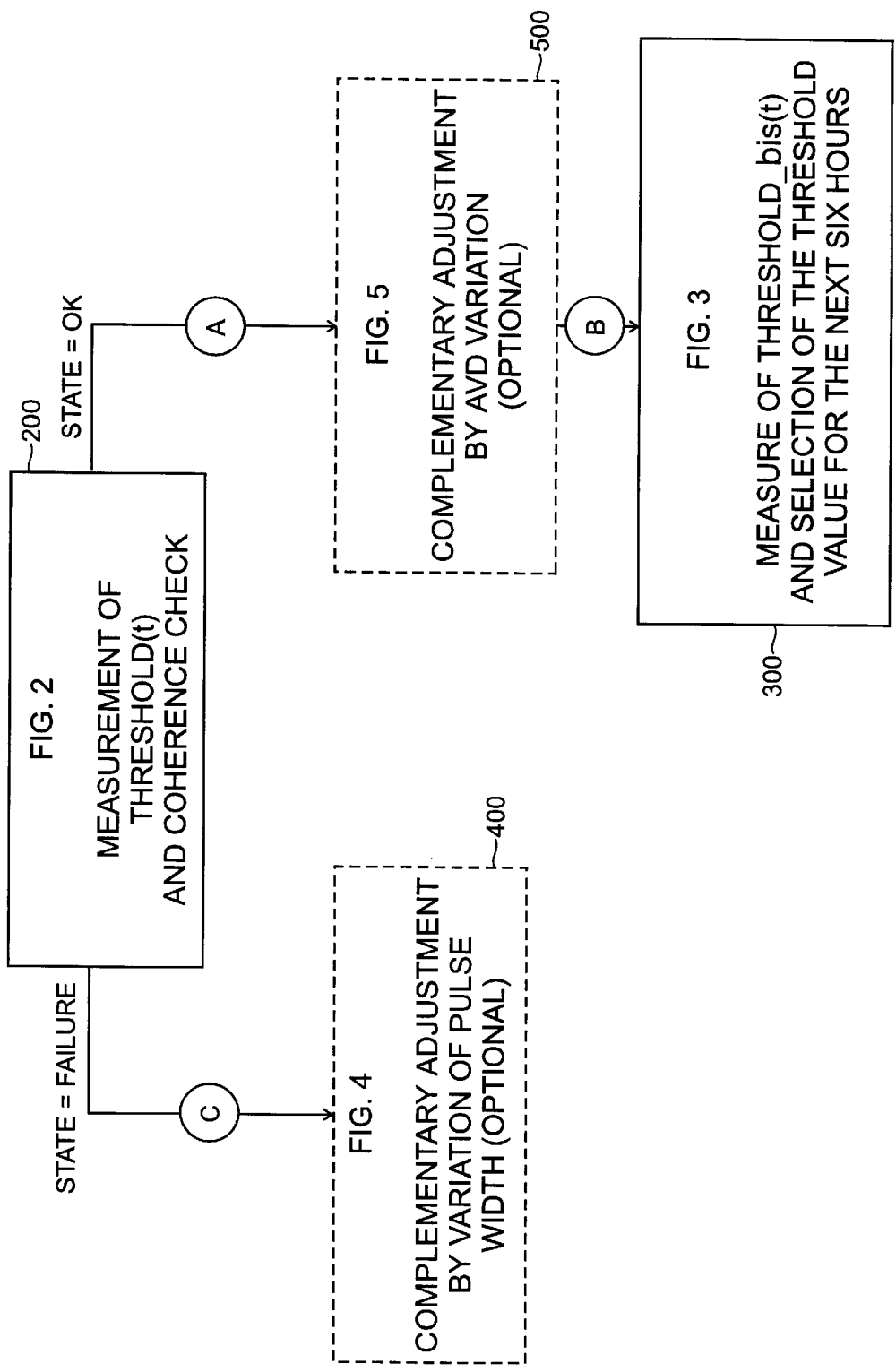
FIG. 1 is a flow chart presenting the various algorithms of the present invention illustrated on FIGS. 2 to 5.
Figure 2:
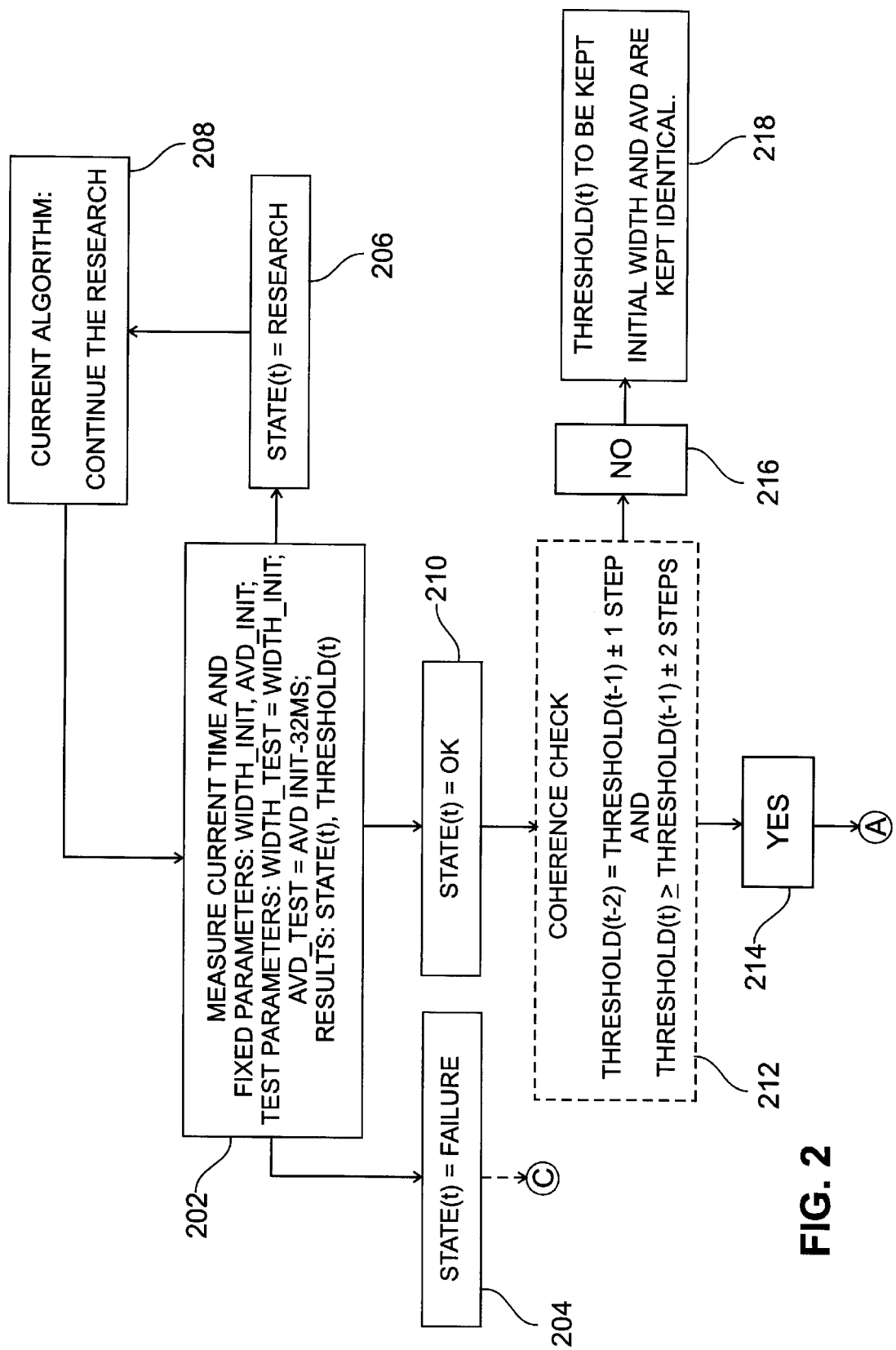
FIG. 2 is a flow chart of capture threshold measurement and coherence check algorithms.

The present invention proposes an improvement to supplement this known algorithm, without modifying it, by providing an additional coherence test (algorithm 200 of FIG. 1, described in detail in FIG. 2). The coherence test, in principle, is directed to confronting each new capture threshold measurement with those given by preceding capture threshold tests.

If the value is considered to be non-coherent, i.e., a positive result, then the test is reiterated, that is, started again a second time (see algorithm 300 of FIG. 1, described in detail in FIG. 3), to establish a capture threshold value (based on either a new value or an old value preserved in memory) for the next period (e.g., six hours) of pacemaker operation. This value to be used is thus established on the basis of a greater number of criteria than in the former known algorithm, and therefore produces a better discernment and a better effectiveness in the field for the stimulation and, especially, for the consumption of the implant device.

In a subsidiary advantageous embodiment, the invention can further improve the algorithm by envisaging a setting of the variation of the pulse duration (algorithm 400 of FIG. 1, described in detail in FIG. 4) and/or of the AVD (algorithm 500 of FIG. 1, described in detail in FIG. 5) throughout the duration of the capture threshold test to improve the analysis qualities of this test.

In the following text and on the FIGS. 1–5, the following definitions will be used:

State(t): the value "FAILURE", "RESEARCH" or "OK" of the indicator returned by the automatic capture threshold test algorithm.

Threshold(t): the last threshold value, i.e., the value measured by the capture threshold test algorithm at the current time t, Threshold(t–1): the penultimate value, measured by the capture threshold test algorithm one test earlier than the current time t, i.e., normally six hours earlier, or less if the algorithm produced an indicator RESEARCH.

Threshold(t–2): the antepenultimate value, i.e., the value measured by the algorithm two tests earlier than the current time t, i.e., normally twelve hours earlier, or less if the algorithm produced an indicator RESEARCH.

State_bis(t): the value of the indicator returned at the current time t but on a reiteration of the test, just after the Threshold(t) measurement (and not six hours afterwards).

Threshold_bis(t): the capture threshold measured at the current time t on a reiteration of the test, just after the Threshold(t) measurement (and not six hours afterwards).

AVD_init: the initial atrio-ventricular delay (AVD) established by the device (typically programmed by the physician, or calculated by various known algorithms which are not the subject of the present invention), before setting of the capture test.

AVD_min: the minimal value of the AVD necessary to be able to launch a threshold test.

AVD_test: the value of the AVD used throughout threshold test.

Width_init: the initial pulse duration established by the apparatus (typically programmed by the physician, or calculated by various known algorithms which are not the subject of the invention), before setting of the capture threshold test; the duration of the pulses (also sometimes called the pulse "width" or pulse "length") is the duration, in milliseconds, of the stimulation pulse delivered by the output circuits of the pulse generator.

Width_min: the minimal value of the pulse width necessary to be able to launch a threshold test.

Width_test: the value of the pulse width used throughout capture threshold test.

Measure of the Threshold and Coherence Check

With reference to FIG. 2, the way in which the threshold is measured, and the way in which the coherence check is carried out, are described.

The first stage, reference 202, concerns launching at the current time t an automatic capture threshold test, by a known process such as that described in the above mentioned U.S. Pat. No. 5,411,533, which is incorporated herein by reference.

At this stage 202, it can be advantageous to systematically reduce the value of the AVD, for example, by 32 ms, throughout the test, to reduce the probability of being in a situation of fusion (i.e., a stimulation concomitant to a spontaneous depolarization). At the end of the test, the AVD is re-programmed to its initially programmed value. This test delivers a value of state indicator State(t), and possibly a threshold value Threshold(t).

If State(t) returns the "FAILURE" indicator (at stage 204), the algorithm can either, in a known manner, automatically fix the stimulation amplitude to the maximum value of 5.0 V for the following six hours, or, preferably and according to an advantageous and subsidiary embodiment of the invention, reiterate the test with a reduced pulse width, as is explained below with reference to FIG. 4.

If State(t) returns the "RESEARCH" indicator (at stage 206), in a traditional manner the algorithm manages this situation while trying to start again the automatic threshold capture test (at step 208).

If State(t) returns the "OK" indicator (at stage 210), the algorithm then carries out a coherence check (at stage 212). This coherence check in the preferred embodiment is operated between the last Threshold(t) value measured at stage 202, the penultimate value Threshold(t−1), and the antepenultimate value Threshold(t−2). More precisely, if: (1) the two values Threshold(t−1) and Threshold(t−2) are close, i.e., if their difference is more or less a measurement step (a measurement step being typically on the order of 0.25 V), and (2) the penultimate value Threshold(t−1) is at least two steps lower than the value of Threshold(t), then it is considered a positive result (i.e., incoherence exists) (at stage 214), and that the Threshold(t) value is overestimated and required to be determined again. It should be understood, of course, that the difference criteria between the thresholds given above is given only as an example, and can be parameterized and modified by the physician as appropriate.

In the contrary case the coherence test gives a negative result (stage 216), and the last Threshold(t) value (measured at stage 202) is regarded as coherent with the penultimate value and the antepenultimate value, and is preserved in memory (stage 218); the level of the stimulation amplitude is thus not modified, and neither are the values of the pulse width nor the AVD value.

Reiteration of the Test

The reiteration of the test is described with reference to FIG. 3. If at stage 212 described above, one has determined that the automatic capture threshold test was to be reiterated, the new test (stage 302) produces a new state indicator State_bis(t), and, eventually, a new capture threshold value Threshold_bis(t).

If the indicator returned by State_bis(t) is "FAILURE" (stage 304) one can either preserve the value Threshold(t) for the six next hours in the same way as in the known algorithm, or, preferably and according to an advantageous and subsidiary improvement of the invention, continue by reiterating the test with a reduced pulse width, as explained below with reference to FIG. 4.

If (stage 306) the indicator returned by State_bis(t) is "RESEARCH" during the next x minutes (x being a preset or a programmable parameter), then the capture threshold previously elected (Threshold(t)) is preserved, as are the initial pulse width and the initial AVD values (stage 308). It is desirable to limit the duration of the research of the Threshold(t) value to a certain time in order to prevent that the algorithm from delivering as a final result a "RESEARCH" indicator with a useless consumption for a hypothetical gain—because in this case the stimulation amplitude will be automatically forced to the maximum value, as indicated above.

If the result of the reiteration of the measurement of the threshold at stage 302 is that the indicator returned by State_bis(t) is "OK" (stage 310), then one compares (stage 312) the new Threshold_bis(t) value with the Threshold(t) value measured just before. If Threshold bis(t)<Threshold (t), then it is considered that Threshold(t) is an aberrant punctual overvaluation and is thus eliminated. If Threshold_bis(t)=Threshold(t), one then considers that the capture threshold really increased by more than two steps in six hours, i.e., there was not an aberrant overvaluation, but instead a correct high evaluation to be taken into account. In one or the other case (stage 314), one preserves the Threshold_bis(t) value for the six next hours, as well as the initial pulse width and AVD (stage 316).

If Threshold_bis(t)>Threshold(t) (stage 318), one considers that the patient presented a rate which does not make it possible to reach useable result, a valid capture threshold having been found with Threshold(t) some cardiac cycles earlier. In this case, one can preserve the last measured value Threshold(t) as final result of the test, with Threshold_bis(t) being regarded as an erroneous result caused by the algorithm and disregarded. Preferably, and according to an advantageous and subsidiary improvement of the invention, one also will seek to continue by reiterating the test on the basis of a reduced AVD, as will be described with reference to the algorithm of FIG. 5.

Modification of the Pulse Width

Figure 4:
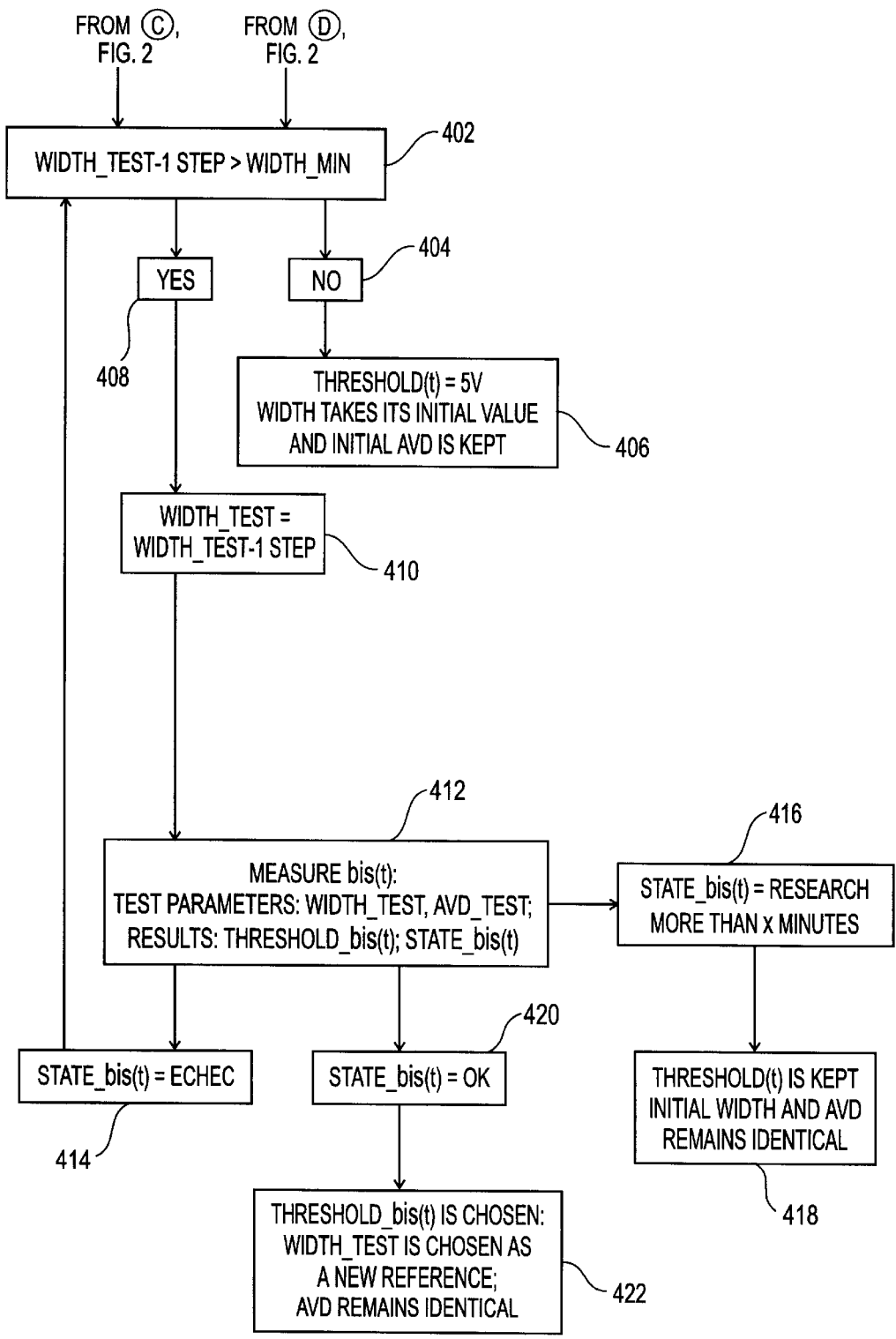
FIG. 4 is a flow chart of the adjustment by variation of the pulse width.

The algorithm shown in FIG. 4 relates to an optional improvement concerning integrating into the capture threshold test algorithm a variation of the pulse width if the indicator returned by State(t) at stage 202, or by State_bis(t) at stage 302, is "FAILURE". The algorithm then will modify the pulse width to try to free itself from the limits of the capture threshold test. Further, if this reduction proves to be beneficial, the algorithm also will reprogram the pulse width to the new value.

At stage 402, one checks first of all if a reduction of pulse width is possible, taking into account the minimal value Width_min programmed in the implant. If this reduction is impossible (stage 404), then one forces the stimulation amplitude to 5.0 V, and the existing pulse width and the initial AVD values are preserved in memory (stage 406).

Figure 3:
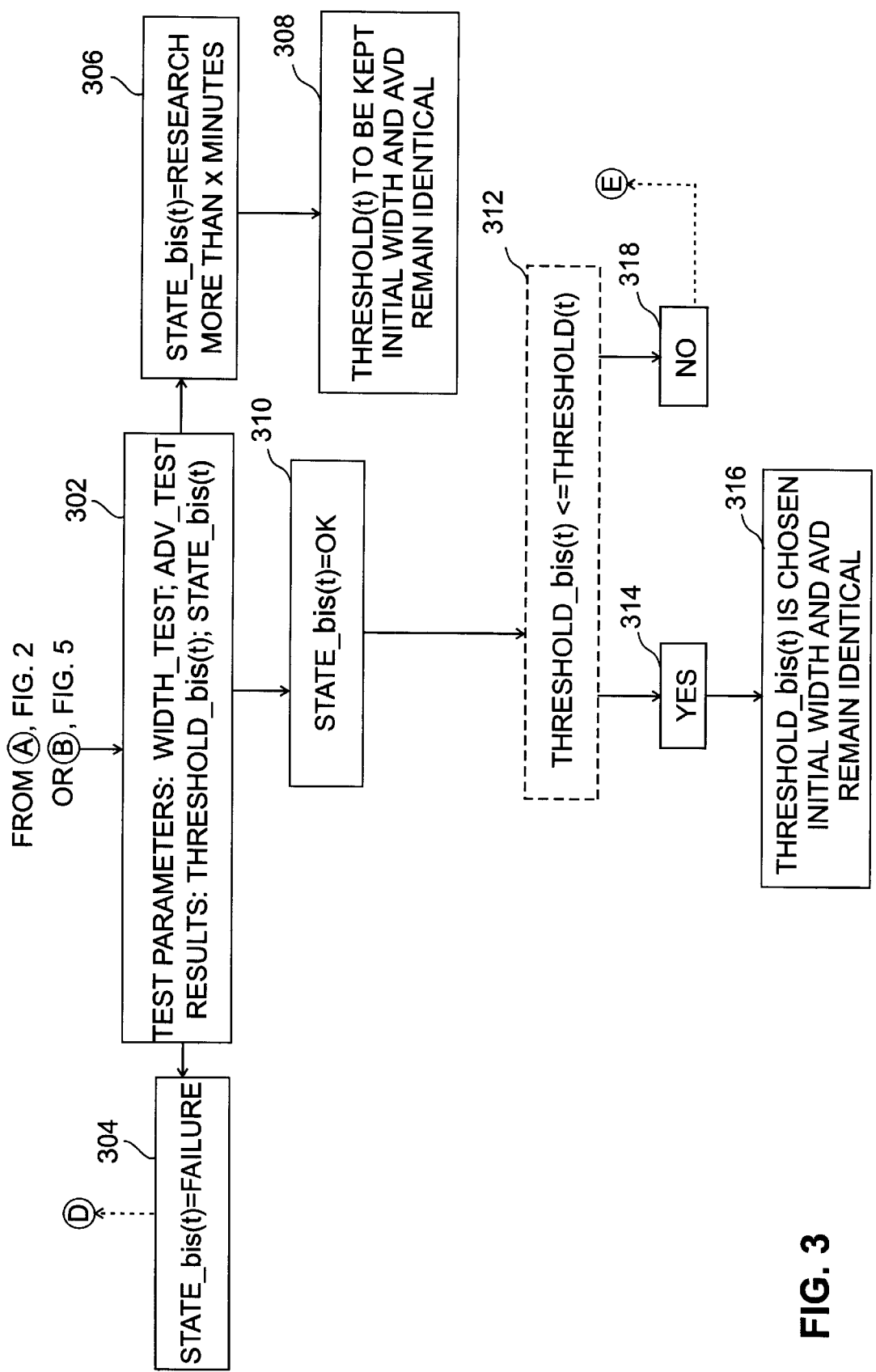
FIG. 3 is a flow chart of the reiteration of the capture threshold measurement and setting of the capture threshold value algorithm.

In the contrary case (stage 408), the pulse width is decreased by one step (stage 410) and one immediately carries out a new capture threshold test (stage 412) with this new Width_test value, in order to determine a new value of the indicator returned by State_bis(t), and, possibly, a new capture threshold value Threshold_bis(t), in the same manner as at stage 302 of FIG. 3. If the indicator of State_bis(t) is "FAILURE" (stage 414), then one will try, returning to stage 402, to reiterate once more the threshold measurement on the basis of a even further reduced pulse width if, of course, a further reduction is possible.

If the indicator returned by State_bis(t) is "RESEARCH" for a length of time greater than x minutes (stage 416), then one preserves the measurement Threshold(t) as the capture threshold value, and preserves the initial pulse width and AVD values (stage 418).

If the indicator returned by State_bis(t) is "OK" (stage 420), then one chooses the value Threshold_bis(t) as the new capture threshold value, and the initial AVD value is preserved. On the other hand, insofar as the modified pulse width gave better results for the capture threshold test, one will select the modified pulse width as a new reference value for future tests.

It will be noted that, in the case where the pulse width was modified, the new value of the capture threshold becomes the new and single reference, the preceding results not being able to be used as a reference because they were carried out with a different pulse width.

Modification of the Duration of the AVD

Figure 5:
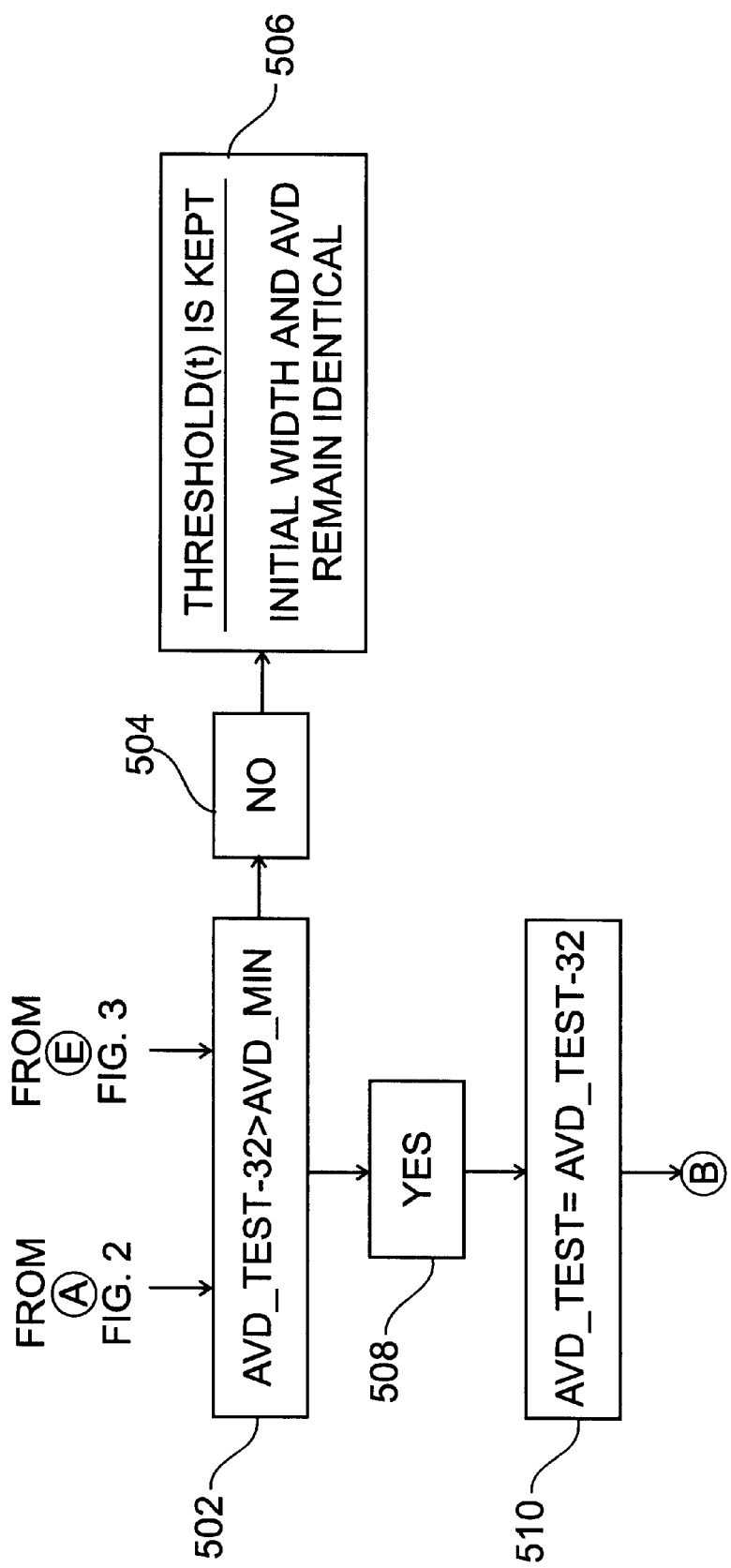
FIG. 5 is a flow chart of the adjustment by variation of the AVD.

The algorithm shown in FIG. 5 relates to an optional improvement concerning integrating into the capture threshold test algorithm a variation of the AVD. In this regard, when the test of stage 312 gives a negative result (stage 318, FIG. 3), i.e., when, in the case of two close measurements of the threshold, the second measurement gives a value greater than the first one, it can be the case of a fusion situation (the stimulation concomitant to a spontaneous depolarization). The reduction of the AVD then offers to the algorithm a chance to anticipate the spontaneous depolarization, and thus to be certain that the test is carried out on a stimulation alone, without a fusion condition. To this end, the algorithm tries to reduce the AVD by a given value, for example, 32 ms.

One checks initially (stage 502), that a reduction of the AVD is possible, i.e., one did not reach the minimal AVD AVD_min programmed in the implant. If the reduction is impossible (stage 504), then one preserves the value of Threshold(t), as well as the initial pulse width and the initial AVD values (stage 506).

If, on the other hand, the reduction is possible (stage 508), then one reduces the AVD (stage 510) by a predetermined value, for example, 32 ms, and one reiterates measurement of Threshold_bis(t) as explained with reference to FIG. 3, but on the basis of this new AVD_test value.

It will be noted that, after complete execution of the algorithm, the AVD always is reset to its initial value, such that the modification occurs only during the capture threshold test. It is thus different from the pulse width, which can be modified not only during the test, but from which the reference value at the end of the algorithm can be different from the values it had at the beginning of the test.

Advantageously, the present invention can be incorporated in an existing implant, such as the Talent pacemaker, controlled by software, the particular functions of the software being put into effect by suitable programming or reprogramming of this software (e.g., downloading by telemetry to the implanted device memory a software routine for performing the stated functions).

One skilled in the art will appreciate that the present invention can be practiced by other than the described embodiments, which are presented for the purposes of illustration and not of limitation.

We claim:

1. An active implantable medical device, comprising:
    stimulation means for delivering pulses heart stimulation pulse of low energy for a treatment of cardiac rate disorders, said pulses having a predetermined amplitude and a predetermined duration, and
    means for adjusting the amplitude of the stimulation pulses, comprising means for automatically measuring capture thresholds, said measuring means operating at predetermined intervals and delivering a measured capture threshold value for use as a basis for the adjustment of the stimulation pulse amplitude;
    wherein the adjusting means further comprises means for validating the capture threshold value, including means for providing a reference value as a function of at least one of the corresponding capture threshold values previously measured, means for performing a coherence test between a last measured capture threshold value and the reference value, said coherence test having one of a positive result and a negative result, and means for inhibiting an adjustment of the stimulation amplitude in response to a positive result of said coherence test.

2. The device of claim 1, wherein said reference value is one of said capture threshold values previously measured.

3. The device of claim 2, wherein the validating means further comprises means for comparing the last measured capture threshold value to the penultimate measured capture threshold value relative to a first predetermined difference, means for comparing a penultimate measured capture threshold value to an ante-penultimate measured capture threshold value relative to a second predetermined difference, and means for providing the positive result of the coherence test when a difference between the last capture threshold value and the penultimate capture threshold value is greater than the first predetermined difference and when the difference between the penultimate threshold value and the ante-penultimate threshold value is less than the second predetermined difference.

4. The device of claim 3, wherein the means for measuring a capture threshold value further comprises step increments and said measuring means further comprises means for measuring the capture threshold values in step increments and each of said first and second predetermined differences is equal to an integer multiple of the step increments.

5. The device of claim 3, wherein the first predetermined difference is greater than or equal to the second predetermined difference.

6. The device of claim 1, further comprising means for reiterating the means for automatically measuring a capture threshold in response to the positive result of the coherence test.

7. The device of claim 6, wherein the adjusting means, after said reiteration, adjusts the stimulation pulse amplitude on the basis of a lowest of the capture threshold values measured before and after said reiteration.

8. The device of claim 6, wherein said stimulation means further comprises an atrio-ventricular delay having a duration and said device further comprises means for operating, in response to the capture threshold measured after a reiteration being greater than the capture threshold measured before said reiteration:
    to reduce the duration of the atrio-ventricular delay, and
    to reiterate a setting of the means for automatically measuring the capture threshold with said reduced atrio-ventricular delay duration.

9. The device of claim 1, wherein the adjusting means further comprises means for determining an impossibility of determining a capture threshold measurement, and further comprising means for operating, in response to the determining means determining an impossibility of determining a capture threshold measurement:
    to reduce a pulse duration of the stimulation pulses, and
    to reiterate a setting of the means for automatically measuring the capture threshold with said reduced pulse duration.

* * * * *

UNITED STATES PATENT AND TRADEMARK OFFICE
CERTIFICATE OF CORRECTION

PATENT NO. : 6,487,451 B1
DATED : November 26, 2002
INVENTOR(S) : Cyril Casset and Jean-Luc Bonnet It is certified that error appears in the above-identified patent and that said Letters Patent is hereby corrected as shown below:

Column 4,
Lines 34 and 47, delete "throughout" and insert -- throughout the -- therefor;

Column 6,
Line 9, delete "reach" and insert -- reach a -- therefor;
Line 12, delete "final" and insert -- the final -- therefor; and Column 7,
Line 42, delete "delivering pulses" and insert -- delivering a -- therefor.

Signed and Sealed this

Thirty-first Day of May, 2005

JON W. DUDAS
*Director of the United States Patent and Trademark Office*